United States Patent [19]

Thompson

[11] 4,038,990
[45] Aug. 2, 1977

[54] CAUTERY PROTECTION CIRCUIT FOR A HEART PACEMAKER

[75] Inventor: David L. Thompson, Fridley, Minn.

[73] Assignee: Medtronic, Inc., Minneapolis, Minn.

[21] Appl. No.: 633,561

[22] Filed: Nov. 19, 1975

[51] Int. Cl.² .............................................. A61N 1/36
[52] U.S. Cl. ............................... 128/419 PG; 333/12
[58] Field of Search .......... 128/2.1 P, 419 P, 419 PG, 128/419 R; 317/53, D6, 33 VR; 333/12, 24.1, 24.2, 76

[56] References Cited

U.S. PATENT DOCUMENTS

| 2,280,950 | 4/1942 | Harder | 333/12 |
| 2,921,275 | 1/1960 | O'Donovan | 333/12 |
| 3,778,759 | 12/1973 | Carroll | 333/12 |
| 3,835,865 | 9/1974 | Bowers | 128/419 PG |

Primary Examiner—William E. Kamm
Attorney, Agent, or Firm—Cameron, Kerkam, Sutton, Stowell & Stowell

[57] ABSTRACT

A cautery protection circuit is disclosed for use with a heart pacemaker or generator circuit and comprises circuit elements for preventing those signals induced within the output portion of the heart pacemaker circuit by an electric field established by cautery procedures, from damaging the generator circuit or turning on the generator circuit at an undesired instant in time, whereby, otherwise, a pacemaker pulse signal may be generated to possibly induce fibrillation within the patient's heart. The cautery protection circuit of this invention is particularly adapted for use with a bipolar heart pacemaker and in particular includes a torroidal inductor having first and second inductors coupled to each of the output leads and having a high permativity coupling therebetween, whereby when cautery signals are induced in the output leads associated with the patient's heart, the coupled inductors operate in a "common mode" configuration to, in effect, "multiply" or increase the inductance presented thereby to the induced signals, thus significantly limiting the current passed therethrough. The coupled inductors of the torroidal inductor also operate in a "differential mode" wherein a pacemaker pulse as generated by the pacemaker generator circuit is applied thereto in a manner such that the fields induced in the coupling between the first and second inductors is opposing, whereby the inductors provide a low or substantially 0 inductance to the pacemaker pulse and thus, impose substantially no shaping upon the output pulses.

1 Claim, 5 Drawing Figures

CAUTERY PROTECTION CIRCUIT FOR A HEART PACEMAKER

CROSS-REFERENCE TO RELATED APPLICATION

Reference is made to the co-pending application entitled, "Cautery Protection Circuit For a Heart Pacemaker," filed Jan. 24, 1975, Ser. No. 543,978, in the name of Joseph A. Ballis, now U.S. Pat. No. 3,968,802.

BACKGROUND OF THE INVENTION

1. Field of the Invention

This invention relates to electronic heart pacing apparatus and in particular to cautery protection circuits associated therewith.

2. State of the Prior Art

Heart pacers such as that described in U.S. Pat. No. 3,057,356 issued in the name of Wilson Greatbatch and assigned to the assignee of this invention, are known for providing electrical stimulus to the heart whereby it is contracted at a desired rate in the order of 72 beats per minute. Such a heart pacemaker is capable of being implanted within the human body and operative in such an environment for long periods of time. Typically, such pacemakers are implanted in the pectorial region or in the abdominal region of the patient by a surgical procedure, whereby an incision is made in such region and the pacemaker with its own internal power supply, is inserted within the patient's body.

In FIG. 1, there is shown an output portion of an electronic heart pacemaker of the prior art. The output circuitry includes a transistor Q12' which is periodically turned on and off at a rate corresponding to that with which the patient's heart is to be stimulated, e.g. 72 beats per minute, and for a duration sufficient to stimulate the patient's heart. The base and collector electrodes are connected respectively to suitable biasing resistor R19', and capacitor C8' and charging resistor R20', and the output is coupled from the collector of the transistor Q12' by a suitable capacitor C8'. A zener diode CR10' is connected across the output of the circuit to provide defibrillation protection. In the normal functioning of the heart, an electrical charge is established across the muscle tissue of the heart, i.e. polarization, and is subsequently discharged, i.e., depolarization. In fibrillation, there are many origins of depolarization which interact with each other and, as a result, the heart assumes a random motion, whereby little if any blood is circulated in the arterial system of the patient. To reinitiate the normal activity of the heart, a defibrillation pulse of relatively large amplitude is applied across the patient's heart. Typically, a pair of paddles (electrodes) is placed on each side of the patient's chest, whereby the defibrillation pulse is applied to his heart to reinitiate the normal rhythmic operation of his heart. The defibrillation pulse as seen by the output portion of the heart pacemaker circuit is in the order of 1500V. It is expected that such a large voltage could easily damage if not destroy the circuit elements of the circuit unless otherwise protected. To prevent this, the zener diode CR10' is inserted across the output, thereby limiting the voltage applied to the pacemaker circuitry to a safe level, e.g. 8V.

The surgical procedure for implanting or removing the heart pacemaker into the body of the patient may involve cauterizing the incision made for the pacemaker pocket, thereby sealing off the small blood vessels surrounding the pocket. In FIG. 2, there is shown a patient with a heart pacemaker 10 implanted therein and the use of a cautery electrode 12 for cauterizing the pacemaker incision. Typically, a cautery unit such as the Bovie Electrosurgical Unit applies an electrical signal such as shown in FIG. 3 to the electrode 12. The high frequency signal has a "damped" waveform; the term "damped" means that the current is in pulses which start with a maximum amplitude and decrease in amplitude at a logrithmic rate. These groups of pulses are sometimes referred to as wave trains and the number of these wave trains occurring per second is called the wave train frequency. The rate at which the pulses occur in each wave train (the number per second) denotes the frequency of the unit, e.g. 500 to 800 kilocycles per second. In the following table, I show values for several characteristics of the two basic currents. The values are approximate, but at the same time representative of current practice.

| CURRENT | OSCILLATING FREQUENCY | WAVE TRAIN FREQUENCY | PEAK OUTPUT VOLTAGE (NO LOAD) | MAXIMUM OUTPUT |
|---|---|---|---|---|
| Cutting | 500–800 KHz | 30000–50000/sec | 3000–3500 volts | 250 watts |
| Coagulating | 500–800 KHz | 10000–15000/sec | 5000–7500 volts | 150 watts |

As shown in FIG. 2, an electric field 18 is established between the cautery electrode or forcep 12 and a cautery ground plate 16 disposed against the patient's buttocks. As shown in FIG. 2, the artificial heart pulse generator 10 and its electrode 14 are disposed in the path of the field 18, whereby a signal is readily induced into the output portion of the heart pacemaker circuitry.

In the above-referenced patent application of Joseph A. Ballis, there is described a cautery protection circuit for use with a heart pacemaker, whereby the effects of signals induced within the output circuit of the heart pacemaker due to an electric field established by cautery procedures, are minimized. As explained in the above-identified patent application, cautery procedures are particularly prone to induce unsymmetrical signals upon the output circuit of unipolar-type heart pacemakers, and such unsymmetrical signals may stimulate the patient's heart into fibrillation. There is shown in FIG. 4 the cautery protection, output circuit as described in the above-identified patent application of Joseph A. Ballis, wherein there is included having an output transistor Q12, and a diode CR14 disposed across the output transistor Q12 in a manner to prevent the output transistor Q12 from being operated in a non-symmetrical manner and tending to render the pacemaker's conduction of cautery induced signals symmetrical, thus reducing the risk of stimulating the patient's heart into fibrillation. Further, the capacitor C8 is connected across the output of the transistor Q12 and is selected to be of such a value to provide a low impedance path to those frequencies as would be induced in the output circuit by the cautery-produced field. Further, zener diodes CR10 and CR12 are connected in-series and in an opposing manner, whereby the heart pacemaker circuitry is protected with respect to relatively large defibrillation pulses. A capacitor C12 is connected in-parallel across the output of the transistor Q12 to detune the resonant circuit formed by the junction capacitances of the diodes CR14, CR10 and CR12, and an inductance L1 disposed in-series between the output circuit and the lead directed therefrom to the patient's heart. The inductance L1 is used as a current-limiting device to reduce the current flow of the high-frequency components that otherwise would be induced therein by cautery procedures.

Typically, the inductor L1 as shown in FIG. 4 is an axial lead, epoxy-molded type inductor having a relatively high DC resistance in the order of approximately 10 ohms. If the impedance of the leads and of their coupling to the heart is in the order of 500 ohms, such an impedance load is not a significant factor. However, if low-threshold leads are used so that the impedance offered by the leads and the heart is in the order of 100 ohms, the resistance offered by such epoxy-molded inductors L1 presents a significant additional load to the heart pacemaker circuit, attenuating its output pulses significantly and placing an undue power drain upon its batteries.

Further, such an inductor typically has an undesired shaping effect upon the pacemaker stimulating signal, having a normally very rapid rise time in the order of 1 $\mu$sec, whereby its pulse rise time is increased by a factor of approximately 8-10. In addition, the inductance L1 may also tend to impose a ringing upon the trailing edge of the pacemaker pulse. This undesirable distortion of the pacemaker pulse may possibly prevent the subsequent monitoring of a heart pacemaker with the use of commonly-available radios. In this regard, it is a common practice for doctors, as well as patients, to monitor the operation of an implanted pacemaker by use of a transistorized radio held next to the patient's body and tuned to a spot on the dial where a radio station normally would not be heard. Such a disposed radio picks up the pacemaker pulses to provide a sound from its speaker in the nature of a "click" upon the occurrence of each pacemaker pulse. The number of such pulses within a minute may be counted to provide an indication of battery life and pacemaker operation. Thus, if the pacemaker output is significantly distorted, the use of such a simple means to monitor the operation of an implanted pacemaker may no longer be available.

SUMMARY OF THE INVENTION

It is therefore an object of this invention to provide a cautery protection circuit for a heart pacemaker capable of significantly limiting the current induced therein by cautery procedures.

It is a further object of this invention to provide a cautery protection circuit for a heart pacemaker that places a significantly less impedance and in particular, inductance upon the heart stimulating output of the pacemaker, whereby the battery life of the pacemaker is extended and the shape of the stimulating pulse is not distorted.

In accordance with the teachings of my invention, first and second inductors are connected in the output circuit of a heart pacemaker circuit for preventing signals induced therein due to the presence of a cautery-induced field, from being applied to the pacemaker circuit. In particular, the inductors have a relatively high coefficient of coupling such that the cautery-induced currents are applied to each of the inductors to induce fields in the inductors in the same direction, thus operating the inductors in a so-called "common mode" to multiply in effect their equivalent inductances and thus limiting the current otherwise applied to the pacemaker circuit. Further, the first and second inductors operate in a so-called "differential mode" to the application of a stimulating pacemaker pulse, whereby the mutual coupling between the first and second inductors is opposing and thus, the inductances thereto are very low, if not substantially 0.

In one particular embodiment of this invention, the coefficient of coupling between the first and second inductors is in the order of 1, and the inductors provide a wide frequency bandwidth in the order of 10 MHz. In particular, the first and second inductors may take the form of torroidal conductors wound about a ferrite core, the core having a permeability of about 120, the torroidal inductor having a resonant frequency in the range of 5-10 MHz. Such a torroidal inductor would have substantially no distortion effect upon the stimulating pulse of the heart pacemaker circuit, but would substantially limit the current applied thereto from cautery-induced signals.

BRIEF DESCRIPTION OF THE DRAWINGS

These and other objects and advantages of the present invention will become more apparent by referring to the following detailed description and accompanying drawings, in which.

DESCRIPTION OF THE PREFERRED EMBODIMENT

Figure 1:
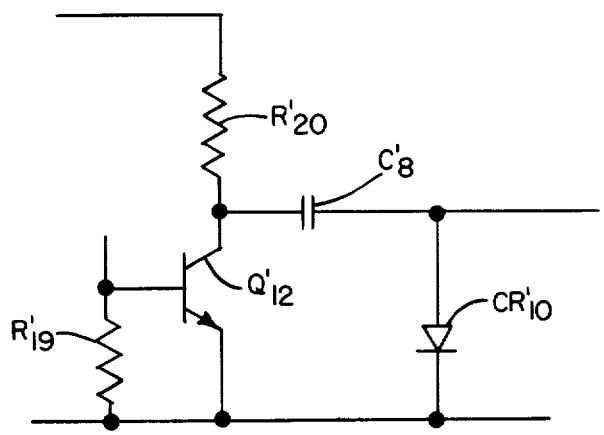
FIG. 1 is a schematic diagram of the output portion of a pacemaker circuit of the prior art.
Figure 2:
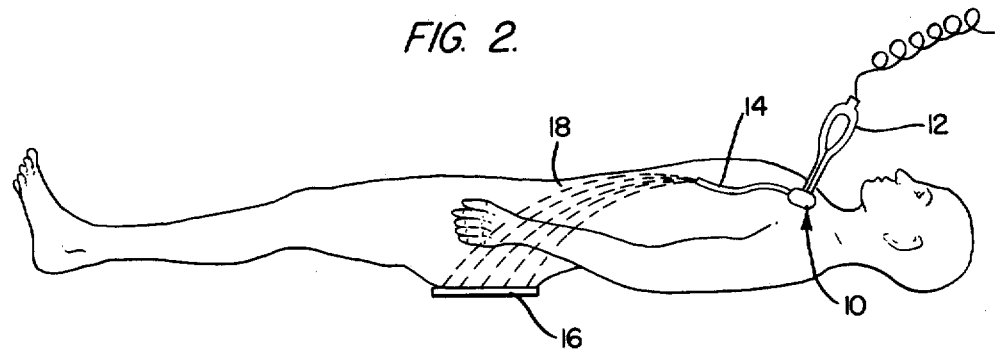
FIG. 2 is an illustration of the relative position of a cautery electrode with respect to a pacemaker pulse generator and lead implanted within a patient.
Figure 3:
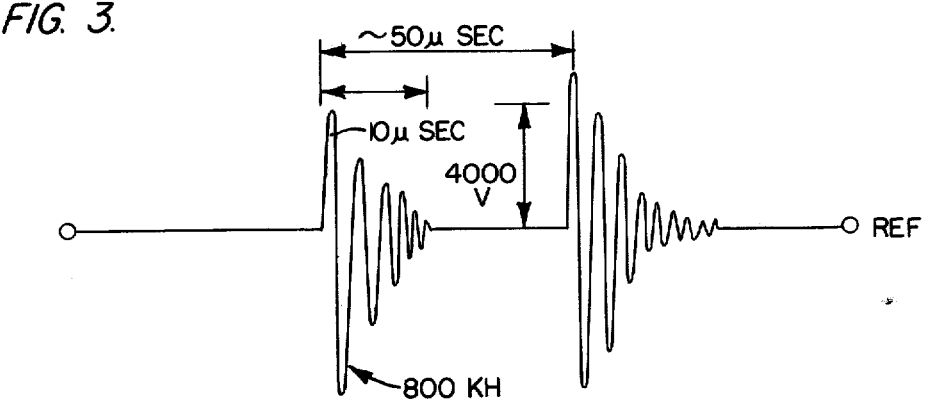
FIG. 3 is a waveform of the output of a typical cautery unit.
Figure 4:
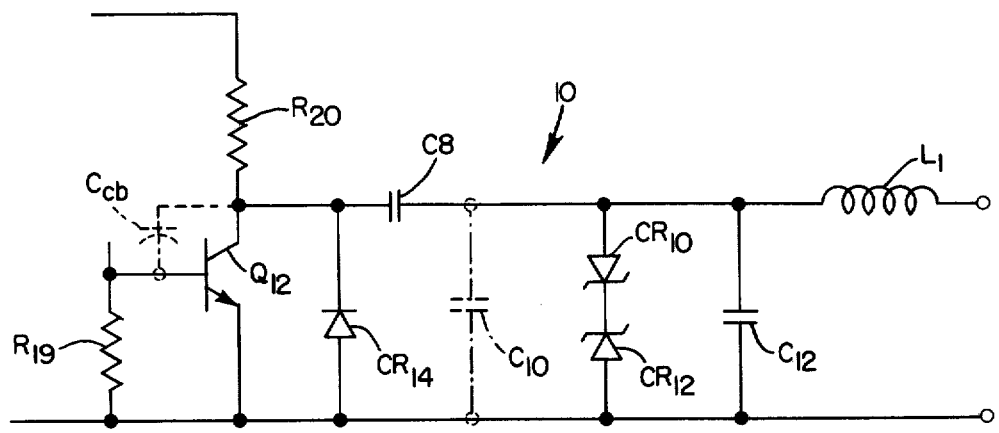
FIG. 4 is a schematic diagram of the output circuit portion of a pacemaker pulse generator circuit of the prior art.
Figure 5:
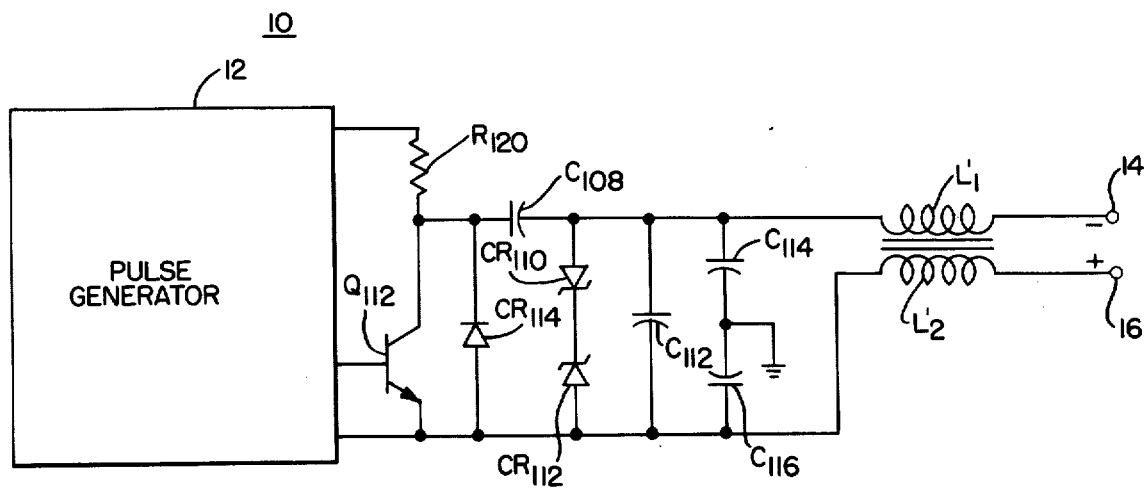
FIG. 5 is a schematic diagram of the output circuit portion of a pacemaker pulse generator circuit in accordance with the teachings of this invention.

Referring now to the drawings and in particular to FIG. 5, there is shown an output portion of a pacemaker circuit 10 in accordance with the teachings of this invention. In particular, the pulse generator containing the batteries and timing control circuitry for generating the stimulating pulses, is represented by the block 12. For a more full disclosure of the details of such circuitry, reference is made to the above-identified application of Joseph A. Ballis and to U.S. Ser. No. 530,799, filed Dec. 9, 1974 in the name of John M. Adams; the aforeidentified applications are incorporated herein specifically by reference. As described, a controlled pulse is applied to the base of an output transistor Q112 rendering it conductive, whereby an output pulse is developed between its emitter and collector portions. An output capacitor C108, typically having a value in the order of 5-20 microfarrads is charged through a resistor R120 to the battery voltage of a value typically in the order of 5.4V. The control pulse applied to the base of transistor Q112 is a squarewave having a pulsewidth in the order of 0.5-1.0 msec, whereby the coupled side of output capacitor C108 is connected to ground, thus placing a negative pulse on the negative terminal 14 having a corresponding pulsewidth and amplitude. The remaining portion of this circuit provides electrocautery, defibrillation and electromagnetic protection. In particular, the zener diodes CR110 and CR112 connected in oppositely-poled fashion, provide defibrillation protection whereby a signal induced by a defibrillation procedure, typically in the order of several hundreds of volts, is effectively clamped to a value in the order of 8V, thus further protecting and preventing breakdown of the circuit capacitors such as capacitors C108 and C112. In addition, capacitors C114 and C116 are connected in-series with each other and across the output of the cautery protection circuit to provide electromagnetic interference protection; typically, these aforementioned capacitors have a value in the order of 1000-5000 picofarrads, such that typical electromagnetic interference in the order of 3 MHz to 2.5 gigahertz is substantially suppressed. In addition, a further capacitor C112 having a value typically in the order of 10,000 picofarrads is also disposed in-parallel across the output of transistor Q112, to attenuate the high-frequency RF signals induced in the circuit output and in addition detunes the resonant circuit established between the capacitances of the aforementioned diodes and the inductance provided by the first and second inductors L1' and L2'. In addition, diode CR114 typically takes the form of a silicon diode that is connected in-parallel across the emitter and collector of transistor Q112 to prevent the currents induced by a cautery procedure from flowing back into the pulse generator 12, possibly damaging the generator 12 and/or causing the transistor Q112 to act as a rectifier, whereby a non-symmetrical signal may be induced through the output leads to the patient's heart, thus possibly causing it to be induced into fibrillation. The portion of the circuit described thus far is substantially identical to that shown in FIG. 4 and described in detail in the above-identified application of Joseph A. Ballis.

In accordance with teachings of this invention, the cautery protection circuit for the pulse generator 12, as shown in FIG. 5, includes first and second inductors L1' and L2' being coupled with each other by a relatively high coefficient of coupling. As can be seen in FIG. 5, the output stimulating signals as derived across the transistor Q112 are applied through the inductors L1' and L2' to the terminals 14 and 16. In turn, a low-impedance lead is connected to the terminals 14 and 16, taking, for example, the form of a coaxial conductor having a spirally-shaped electrode for insertion into the myocardium of the patient's heart and an annular plate electrode disposed thereabout, whereby an effective low impedance connection may be made thereby to the heart. Such a lead is more fully described in co-pending applications Ser. No. 610,063, "Bipolar Body Tissue Electrode," filed in the names of R. H. Rockland and D. H. Gobeli. Other endocardial and myocardial leads could, of course, be substituted for this specifically described lead.

In one illustrative embodiment of this invention, the inductors L1' and L2' take the form of a torroidal inductor custom manufactured to meet the specifications described herein. The inductors L1' and L2' may be wound in a bifilar, segmented or layered manner about a torroidal, ferrite core. Typically, such a component is quite small, thereby readily being incorporated into a pacemaker circuit, wherein size and compactness are of prime concern because of implantation within the patient's body. Further, the number of windings of such an inductor are relatively smaller, thereby reducing accordingly the resistance provided by the inductors L1' and L2' making up such a torroidal inductor. As a result, the resistance presented by the inductances L1' and L2' may be reduced by a factor of 10, thereby reducing the attenuation of the pacemaker's pulses, as well as the drain placed upon the pacemaker batteries. Further, it is desired that there be efficient coupling between the inductors L1' and L2' in the form of a core having a permeability in the order of 120. Further, such a torroidal inductor should have a very wide bandwidth in the order of 10 MHz as well as an extremely high resonant frequency in the range of 5-10 MHz or greater. As a result of the relatively wide bandwidth and the high resonant frequency characteristics, the signals as applied therethrough to the lead attached to the patient's heart, are not shaped or otherwise distorted.

The significance of incorporation of a torroidal inductor into the cautery protection circuit as shown in FIG. 5, is more fully realized in connection with the operation of this circuit and in particular the torroidal inductor. In particular, during a cautery procedure and in the presence of the cautery-induced field, relatively high voltage or high-current signals may be applied simultaneously through the lead to the terminals 14 and 16. As a result, high currents are induced substantially simultaneously through each of the inductors L1' and L2' in the same direction. As a result, the torroidal inductor operates in a "common mode" wherein lines of field are induced by each of the aforementioned inductors in the same direction through their coupling, thereby tending to increase or effectively "multiply" the inductance offered by each of the inductors L1' and L2'. As a result, as the frequency of the induced signals increases, the inductances of inductors L1' and L2' increase, thereby tending to limit the current that may be passed to the remainder of the cautery protection circuit as well as to the pulse generator 12.

On the other hand, when the transistor Q112 is turned on to generate a pacemaker pulse, the signal is applied through the inductor L1' to the negative terminal 114 and from the positive terminal 116 to the inductor L2', whereby the lines of field established within the coupling between the aforementioned inductors are in a cancelling direction and the inductance offered to the pacemaker pulse is significantly reduced. As a result of operating in the above-described differential mode, a very small if not substantially 0 inductance, if offered to the pacemaker pulse, and as a result, the pacemaker pulse is not shaped or otherwise distorted by such an inductance. Thus, the cautery protection circuit of FIG. 5 is particularly adapted for operation with a bipolar pacemaker, wherein a torroidal inductor is included and is operative in a "common or blocking mode" to substantially attenuate the current passing from the output terminals to the pulse generator as is induced therein by cautery procedures. On the other hand, the torroidal inductor also is operative in a "differential mode," whereby the output of the pulse generator in the form of pulses is applied therethrough with a minimum of shaping or other distortion, in that in this mode, the torroidal inductor offers little or substantially no inductance to the pulse generator output. As a result, the shape of the pacemaker pulses in terms of rapid rise time and lack of ringing at the trailing edge thereof is achieved, while offering a very low resistance.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A bipolar heart pacemaker circuit comprising:
   a. a pulse generator for generating a control signal at a desired rate according to that with which it is desired to stimulate a patient's heart;
   b. output switch means responsive to the control signal for providing a heart stimulating output pulse to be applied by first and second leads to the patient's heart; and
   c. a torroidal inductor including first and second inductors, each connected in-series with a corresponding one of said first and second leads and coupled together by a high coefficient of coupling to operate in a first mode in the presence of a cautery-inducted field, wherein the signals applied to said first and second inductors by the cautery-induced field induce fields in the same direction through said coupling and the inductances offered to the cautery-induced signals are correspondingly increased, and in a second, differential mode in response to the application of a pacemaker pulse signal wherein opposing fields are established through said coupling between said first and second inductors so that the inductances offered by said first and second inductors are significantly reduced, said torroidal inductor comprising a torroidal core having permeability in the order of 120, a bandwidth of not less than 10MHz and a resonant frequency of not less than 5MHz, whereby the impedance presented to said pulse generator is reduced and distortion applied to the heart stimulating output pulse is reduced.

* * * * *